United States Patent [19]

Steiner et al.

[11] Patent Number: 5,703,091
[45] Date of Patent: Dec. 30, 1997

[54] N-SUBSTITUTED AZABICYCLOALKANE DERIVATIVES, THEIR PREPARATION AND USE

[75] Inventors: Gerd Steiner, Kirchheim; Rainer Munschauer, Neustadt; Liliane Unger, Ludwigshafen; Hans-Jürgen Teschendorf, Dudenhofen; Thomas Höger, Edingen-Neckarhausen, all of Germany

[73] Assignee: BASF Aktiengesellschaft, Ludwigshafen, Germany

[21] Appl. No.: 656,240

[22] PCT Filed: Nov. 26, 1994

[86] PCT No.: PCT/EP94/03913

§ 371 Date: Jun. 6, 1996

§ 102(e) Date: Jun. 6, 1996

[87] PCT Pub. No.: WO95/15327

PCT Pub. Date: Jun. 8, 1995

[30] Foreign Application Priority Data

Dec. 4, 1993 [DE] Germany ............... 43 41 403.6

[51] Int. Cl.$^6$ ............... A61K 31/39
[52] U.S. Cl. ............ 514/300; 514/302; 514/412; 546/113; 546/115; 548/452; 548/453
[58] Field of Search ............ 514/412, 300, 514/302; 548/452, 453; 546/113, 115

[56] References Cited

U.S. PATENT DOCUMENTS 4,308,387  12/1981  Bjoerk et al. .
4,435,419  3/1984  Epstein et al. ............ 514/412
4,605,655  8/1986  Yevich et al. .
5,216,018  6/1993  Ciganek .
5,532,243  7/1996  Gilligan ............ 514/412

FOREIGN PATENT DOCUMENTS 190 472    8/1986    European Pat. Off. .
400 661    12/1990   European Pat. Off. .
410 114    1/1991    European Pat. Off. .
1 289 845  2/1969    Germany .
29 41 880  4/1989    Germany .

OTHER PUBLICATIONS

Chem. Abst. vol. 92, 1980, p. 584.
Chem Abst. vol. 108, 1988, p. 616.
Chem Abst. vol. 93, 1980, p. 649.
Chem. Abst. vol. 81, 1974, p. 323.
WO 94/00458.
WO 92/18480.

*Primary Examiner*—James H. Reamer
*Attorney, Agent, or Firm*—Keil & Weinkauf

[57] ABSTRACT

Compounds of the formula I

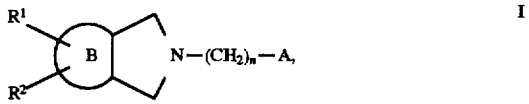

where B, $R^1$, $R^2$, n and A have the meanings given in the description, and their preparation are described. The novel compounds are suitable for the control of diseases.

3 Claims, No Drawings

N-SUBSTITUTED AZABICYCLOALKANE DERIVATIVES, THEIR PREPARATION AND USE

The invention relates to novel N-substituted azabicycloalkane derivatives, their preparation and use for preparing pharmaceutical active compounds.

It has been disclosed that basically substituted butyrophenone derivatives or benzamide derivatives have neuroleptic or cerebro-protective activity (U.S. Pat. No. 4,605, 655, EP 410 114, DE 12 89 845, EP 400 661, DE 29 41 880, EP 190 472, DE 42 19 973).

The observed high affinities to dopamine and serotonin receptor subtypes appear to play a particular role in this context.

It has now been found that N-substituted 3-azabicycloalkane derivatives of the formula I

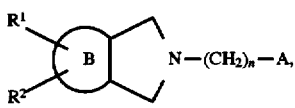

where
- B is a 3-, 5- or 6-membered ring which can contain 1 nitrogen atom and/or 1 oxygen atom and possibly one double bond,
- $R^1$ is a phenyl group which is unsubstituted or mono- or disubstituted by halogen atoms or $C_1$–$C_4$-alkyl, trifluoromethyl, hydroxyl, $C_1$–$C_4$-alkoxy, amino, monomethylamino, dimethylamino, cyano or nitro groups,
- $R^2$ is a hydrogen atom, a $C_1$–$C_4$-alkyl radical, or a phenyl group which is unsubstituted or substituted by halogen, methoxy, hydroxyl or amino,
- n is the number 0, 1, 2, 3 or 4,
- A is a hydrogen atom or one of the radicals —CO—$R^5$ or —$NR^6$—CO—$R^7$,
- $R^5$ is a phenyl group which is unsubstituted or mono- or disubstituted by fluorine, chlorine, bromine or a hydroxyl, nitro, amino, $C_{1-4}$-alkanoylamino, $C_{1-4}$-alkylamino, $C_1$–$C_4$-alkyl or methoxy group or a naphthyl group which is unsubstituted or substituted by fluorine or chlorine,
- $R^6$ is a hydrogen atom or a methyl group, and
- $R^7$ is a phenyl group which is mono- or disubstituted by fluorine, chlorine, bromine, $C_1$–$C_4$-alkyl, hydroxyl or methoxy or monosubstituted by nitro, cyano, trifluoromethyl, amino, $C_1$–$C_4$-alkylamino or di-$C_1$–$C_4$-alkylamino or a thienyl, naphthyl, benzothienyl or indenyl group which is unsubstituted or substituted by fluorine, chlorine or nitro, and their salts with physiologically tolerable acids, have useful pharmacological properties.

In the formula I, the substituents $R^1$ to $R^6$ and n preferably have the following meanings:

- $R^1$: phenyl, unsubstituted or substituted by fluorine, chlorine, methoxy, trifluoromethyl, nitro, hydroxyl or amino,
- $R^2$: hydrogen, methyl,
- n: 2 or 3,
- $R^5$: p-fluorophenyl, phenyl, p-chlorophenyl, 1-naphthyl,
- $R^6$: hydrogen,
- $R^7$: phenyl, p-fluorophenyl, o-aminophenyl, o-N-methylaminophenyl, 5-chlorothien-1-yl, 1-naphthyl, 3-indenyl, 3-chloro-1-benzothien-2-yl.

The bicyclic ring system in the left moiety of the formula I is particularly

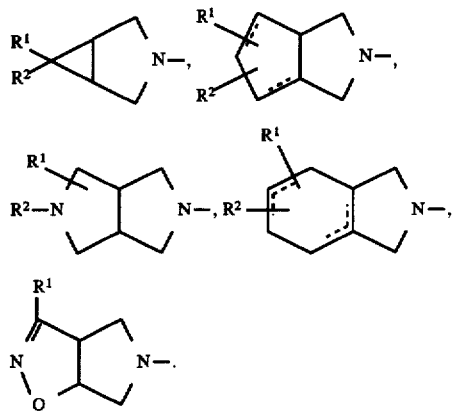

Preferred compounds are in particular those where
- $R^1$ is phenyl which is preferably substituted in the p-position by fluorine or chlorine or in the m-position by fluorine or chlorine and
- $R^2$ is hydrogen or methyl.

The compounds of the formula I according to the invention can be prepared by reacting a compound of the formula II

where A and n have the meanings given and Nu is a nucleofugic leaving group, with a 3-azabicycloalkane derivative of the formula III

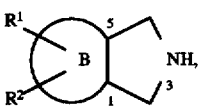

where B, $R^1$ and $R^2$ have the meaning given above, removing any protective groups present and if desired converting the compound thus obtained into the acid addition salt of a physiologically tolerable acid.

Suitable nucleofugic leaving groups for Nu are preferably halogen atoms, in particular bromine or chlorine.

The reaction is expediently carried out in the presence of an inert base, such as triethylamine or potassium carbonate, as acid acceptor in an inert solvent, such as a cyclic saturated ether, in particular tetrahydrofuran or dioxane, or a benzene hydrocarbon, such as toluene or xylene.

The reaction is in general carried out at from 20° to 150° C., in particular from 80° to 140° C., and is in general complete within from 1 to 10 hours.

The compounds of the formula I according to the invention can either be purified by recrystallization from the customary organic solvents, preferably from a lower alcohol, such as ethanol, or by column chromatography.

Racemates can be resolved into the enantiomers in a simple manner by classical cleavage using optically active carboxylic acids, e.g. tartaric acid derivatives, in an inert solvent, e.g. lower alcohols.

The free 3-azabicycloalkane derivatives of the formula I can be converted to the acid addition salt of a pharmacologically tolerable acid in a customary manner, preferably by treating a solution with an equivalent of the corresponding acid. Pharmaceutically tolerable acids are, for example, hydrochloric acid, phosphoric acid, sulfuric acid, methanesulfonic acid, sulfamic acid, maleic acid, fumaric acid, oxalic acid, tartaric acid or citric acid.

The compounds according to the invention have useful pharmacological properties. They can be used as neuroleptics (in particular atypical), antidepressants, sedatives, hypnotics, CNS protectants or muscle relaxants. Several of the active qualities can occur in combination in one compound according to the invention. Demonstration of the pharmacological action is carried out both in vivo and in vitro, substance characterization in particular being possible as a result of the in some cases very high and selective affinity to receptor subtypes, e.g. dopamine $D_1$, $D_2$, $D_3$ and especially $D_4$ receptors; serotonin 1A, 1D and 2 receptors, alpha 1 and 2 receptors; histamine 1 and muscarine receptors.

The following methods were used for the in vivo characterization:

a) Effect on orientation motility

In a new environment, mice show increased exploratory behavior which is manifested by increased motor activity. This motor activity is measured in light barrier cages for 0–30 min after the animals (female NMRI mice) have been placed in the cages.

ED50: dose which reduces the motor activity by 50% in comparison with placebo-treated controls.

b) Apomorphine antagonism

Female NMRI mice receive 1.21 mg/kg of apomorphine s.c. At this dose, apomorphine leads to motor activation which is manifested by continuous climbing when the animals are kept in wire mesh cages. The climbing is assessed using a score (every 2 min for 30 min):

0: animal has four paws on the floor

1: animal has two paws on the wire

2: animal has four paws on the wire (is climbing).

The climbing behavior can be inhibited by pretreatment with antipsychotics.

ED50: dose which inhibits the climbing activity of the animals by 50% in comparison with placebo-treated controls.

c) Methamphetamine antagonism

Female NMRI mice receive 1 mg/kg of methamphetamine p.o. and, after 30 min, are placed in light barrier cages to measure the motor activity (2 animals/cage, 4 cages/dose). The test substances are given orally 30 min before methamphetamine. The increase in activity due to methamphetamine is calculated for the period 15 to 60 min after the animals have been placed in the measurement cages as the difference between methamphetamine controls and placebo controls and set equal to 100%. The ED100 is the dose of the test substance which completely abolishes the increase in activity.

d) L-5-HTP antagonism

Female Sprague-Dawley rats receive L-5-HTP in a dose of 316 mg/kg i.p. The animals subsequently develop an excitation syndrome of which the symptoms forepaw treading and tremor are assessed with the aid of a score (0=not present, 1=moderate, 2=clearly marked) every 10 min in the period from 20 to 60 min after L-5-HTP administration. On average, a score of 17 is achieved after L-5-HTP administration. The test substances are given p.o. 60 min before L-5-HTP. The ED50 is calculated as the dose which on average decreases the control score by 50%.

The methods mentioned are suitable for characterizing substances as antipsychotics; in particular, the inhibition of motor stimulation induced by methamphetamine is regarded as predictive of an antipsychotic effect. A serotonin-antagonistic effect may be shown by the inhibition of the L-5-HTP syndrome, a type of effect which is characteristic of the atypical neuroleptics.

The novel compounds show a good effect in these tests.

The invention accordingly also relates to a therapeutic composition, which contains a compound of the formula I or its pharmacologically tolerable acid addition salt as active compound in addition to customary excipients and diluents, and the use of the novel compounds in the control of diseases.

The compounds according to the invention can be administered in a customary manner orally or parenterally, intravenously or intramuscularly.

The dosage depends on the age, condition and weight of the patient and on the mode of administration. As a rule, the daily dose of active compound is from about 1 to 100 mg/kg of body weight on oral administration and from 0.1 to 10 mg/kg of body weight on parenteral administration.

The novel compounds can be used in conventional solid or liquid pharmaceutical administration forms, e.g. as tablets, film tablets, capsules, powders, granules, coated tablets, suppositories, solutions, ointments, creams or sprays. These are prepared in a customary manner. The active compounds can in this case be processed with the customary pharmaceutical auxiliaries such as tablet binders, fillers, preservatives, tablet disintegrants, flow regulators, plasticizers, wetting agents, dispersants, emulsifiers, solvents, release-delaying agents, antioxidants and/or propellant gases (cf. H. Sucker et al.: Pharmazeutische Technologie [Pharmaceutical Technology], Thieme-Verlag, Stuttgart, 1978). The administration forms thus obtained normally contain the active compound in an amount from 1 to 99% by weight.

The substances of the formulae II and III required as starting substances for the synthesis of the novel compounds are known or can be synthesized from similar starting materials according to the preparation methods described in the literature.

The following examples serve to illustrate the invention:
Preparation of the precursors A. exo-2-Phenyl-3-methyl-1,5-cis-3,7-diazabicyclo[3.3.0] octane a) 6-Phenyl-7-methyl-1,5-cis-3,7-diazabicyclo[3.3.0] octane-2,4-dione 17.8 g (200 mmol) of sarcosine, 15.2 ml (150 mmol) of benzaldehyde and 9.7 g (100 mmol) of maleimide were suspended in 500 ml of toluene and refluxed in a Dean and Stark apparatus for 3 h. A further 17.8 g (200 mmol) of sarcosine and 15.2 ml (150 mmol) of benzaldehyde were then added and the mixture was refluxed for a further hour. After cooling, 50 g of sodium sulfate were added, stirred for a few minutes and filtered off. The filtrate was concentrated and the residual viscous oil (37.2 g) was purified by column chromatography (silica gel, eluent dichloromethane/methanol 98:5). In this manner, 4.2 g (18%) of enriched endo adduct (endo:exo=80:20) and 10.7 g (47%) of enriched exo adduct (exo:endo=80:20) were obtained.

b) exo-2-Phenyl-3-methyl-1,5-cis-3,7-diazabicyclo [3.3.0]octane

A solution of 8.5 g (37 mmol) of enriched exo-6-phenyl-7-methyl-1,5-cis-3,7-diazabicyclo[3.3.0]octane-2,4-dione in 130 ml of absolute tetrahydrofuran was added dropwise at room temperature with good stirring in the course of 25 min to a suspension of 7.0 g (185 mmol) of lithium aluminum hydride in 180 ml of absolute tetrahydrofuran. After the slightly exothermic reaction had subsided, the mixture was stirred at room temperature for a further 18 h. While cooling in ice, 70 ml of ten percent sodium hydroxide solution were then added dropwise with vigorous stirring and the mixture was allowed to come to room temperature with stirring. The precipitated hydroxides were filtered off with suction and washed several times with tetrahydrofuran, and the combined filtrates were concentrated. 6.3 g (84%) of a pale oil were isolated.

B. endo-2-Phenyl-3-methyl-1,5-cis-3,7-diazabicyclo[3.3.0]octane

In a similar manner to procedure A.b), 3.0 g (81%) of cloudy oil were obtained from 4.2 g (18 mmol) of enriched endo-6-phenyl-7-methyl-1,5-cis-3,7-diazabicyclo[3.3.0]octane-2,4-dione and 3.5 g (91 mmol) of lithium aluminum hydride.

C. 3-Phenyl-1,5-cis-3,7-diazabicyclo[3.3.0]octane a) 7-Benzyl-3-phenyl-1,5-cis-3,7-diazabicyclo[3.3.0]octane-2,4-dione 20.1 g (100 mmol) of N-benzylglycine hydrochloride, 7.5 g (250 mmol) of paraformaldehyde and 8.7 g (50 mmol) of N-phenylmaleimide were suspended in 500 ml of toluene and 17.4 ml (100 mmol) of N-ethyldiisopropylamine were finally added. The reaction mixture was refluxed for 30 min in a Dean and Stark apparatus and then filtered through sodium sulfate, and the filtrate was concentrated. The residual viscous oil (18.6 g) was purified by column chromatography (silica gel, eluent dichloromethane). 8.7 g (56%) of a pale oil were obtained.

b) 7-Benzyl-3-phenyl-1,5-cis-3,7-diazabicyclo [3.3.0]octane

A solution of 8.7 g (28 mmol) of 7-benzyl-3-phenyl-1,5-cis-3,7-diazabicyclo[3.3.0]octane-2,4-dione in 100 ml of absolute tetrahydrofuran was slowly added dropwise at room temperature to a suspension of 2.65 g (71 mmol) of lithium aluminum hydride in 75 ml of absolute tetrahydrofuran. The mixture was then stirred under reflux for a further 2 h. Then, while cooling in ice, 30 ml of ten percent sodium hydroxide solution were slowly added dropwise, and the precipitated hydroxides were filtered off with suction. Washing with tetrahydrofuran and concentration of the combined filtrates afforded 7.2 g of a cloudy oil, which was purified by column chromatography (silica gel, dichloromethane/methanol 97:3). Yield: 5.8 g (73%) of clear oil.

c) 3-Phenyl-1,5-cis-3,7-diazabicyclo[3.3.0]octane 5.8 g (21 mmol) of 7-benzyl-3-phenyl-1,5-cis-3,7-diazabicyclo[3.3.0]octane were dissolved in 170 ml of methanol, and 0.7 g of palladium on carbon (10%) was added. A solution of 6.6 g (104 mmol) of ammonium formate in 7 ml of water was then added dropwise with stirring. The mixture was then stirred for 3 h at 50° C., a further 0.5 g of palladium on carbon (10%) was subsequently added, and the mixture was stirred for a further hour at 50° C. The catalyst was filtered off with suction and washed well with methanol, and the combined filtrates were concentrated to dryness. The residue was taken up in water, adjusted to pH 9–10 and extracted three times with dichloromethane. Drying and concentration of the organic phase afforded 3.0 g of white solid, which was digested in a little ether. Filtering off with suction and drying yielded 1.7 g (43%) of colorless, fine crystals.

D. exo-6-Phenyl-3-azabicyclo[3.1.0]hexane a) cis-1,2-bis(Hydroxymethyl)trans-3-phenylcyclopropane A solution of 20.0 g (85 mmol) of dimethyl trans-3-phenyl-cis-1,2-cyclopropanedicarboxylate in 250 ml of absolute tetrahydrofuran was slowly added dropwise to a suspension of 7.9 g (213 mmol) of lithium aluminum hydride in 150 ml of absolute tetrahydrofuran while cooling in ice at 0° C. The mixture was slowly allowed to come to room temperature and was stirred for 18 h. Then, 70 ml of ten percent sodium hydroxide solution were slowly added dropwise while cooling in ice, and the precipitated hydroxides were filtered off with suction and washed with tetrahydrofuran. Concentration of the filtrate yielded 14.7 g (97%) of viscous, yellow oil.

b) cis-1,2-bis(Methanesulfonyloxymethyl)trans-3-phenylcyclopropane

A solution of 14.7 g (82 mmol) of cis-1,2-bis(hydroxymethyl)trans-3-phenylcyclopropane in 70 ml of absolute pyridine was added dropwise at −5° C. to a solution of 32.2 g (281 mmol) of methanesulfonyl chloride in 350 ml of absolute pyridine such that the internal temperature did not rise above 0° C. and the mixture was stirred for a further 3 h at −5° C. The cold reaction mixture was then poured onto ice-water to which 60 ml of conc. sulfuric acid had previously been added. The mixture was stirred for a further 1 h, and the supernatant solution was decanted from the oily precipitate deposited, the latter was taken up in a little dimethylformamide and this solution was poured onto ice-water with stirring. After stirring for 1 h, the fine crystalline precipitate was filtered off with suction, washed with water and dried. 19.6 g (78%) of pale powder were obtained.

c) 3-(4-Methoxyphenylmethyl)exo-6-phenyl-3-azabicyclo[3.1.0]hexane 5.0 g (16.6 mmol) of cis-1,2-bis(methanesulfonyloxymethyl)-trans-3-phenylcyclopropane were introduced into 6.8 g (50 mmol) of 4-methoxybenzylamine and the mixture was heated at 100° C. for 2 h with good stirring. After cooling, the mixture was dissolved in methylene chloride, and the organic phase was washed twice with water and concentrated after drying with sodium sulfate. The crude product (4.9 g) was purified by column chromatography (silica gel, eluent methylene chloride/methanol 99:1). 2.2 g (48%) of product were isolated as a yellow oil.

d) exo-6-Phenyl-3-azabicyclo[3.1.0]hexane 2.2 g (7.9 mmol) of 3-(4-methoxyphenylmethyl)exo-6-phenyl-3-azabicyclo[3.1.0]hexane were dissolved in 70 ml of methanol and 0.6 g of palladium on carbon (10%) was added. A solution of 2.5 g (39 mmol) of ammonium formate in 3 ml of water was then added dropwise with stirring. The mixture was then stirred for 1 h at 50° C. The catalyst was filtered off with suction and washed well with methanol, and the combined filtrates were concentrated to dryness. The residue was taken up in water, adjusted to pH 9–10 and extracted three times with dichloromethane. Drying and careful concentration of the organic phase at a maximum bath temperature of 30° C. afforded 1.1 g (88%) of product as a yellow oil.

E. 6-(4-Fluorophenyl)-1,5-cis-3-azabicyclo[3.3.0]oct-6-ene a) 3-Benzyl-6-(4-fluorophenyl)-6-hydroxy-1,5-cis-3-azabicyclo[3.3.0]octane First 1.4 g (56 mmol) of magnesium turnings and then a solution of 9.4 g (54 mmol) of 4-bromo-1-fluorobenzene in 55 ml of absolute tetrahydrofuran were added dropwise under nitrogen to 20 ml of absolute tetrahydrofuran. After the weakly exothermic reaction had subsided, the mixture was stirred for a further 1 h. A solution of 10.5 g (49 mmol) of 3-benzyl-6-oxo-1,5-cis-3-azabicyclo[3.3.0]octane (K. Miyajima, M. Takemoto and K. Achiwa, Chem. Pharm. Bull. 39 (1991), 3175) in 40 ml of absolute tetrahydrofuran was then added dropwise and the mixture was subsequently refluxed for 5 h. 50 ml of a saturated ammonium chloride solution were then added dropwise while cooling in ice, and the precipitated hydroxides were filtered off with suction and washed with tetrahydrofuran. The combined filtrates were concentrated, and the residue was taken up in water, adjusted to pH 11 with ten percent sodium hydroxide solution and extracted twice with dichloromethane. The organic phase was washed once with saturated sodium chloride solution, dried over sodium sulfate and concentrated. The residual oil (14.8 g) was purified by column chromatography (silica gel, eluent dichloromethane/methanol 98.5:1.5). 11.5 g (75%) of yellow oil were obtained.

b) 6-(4-Fluorophenyl)-6-hydroxy-1,5-cis-3-azabicyclo[3.2.0]octane 9.0 g (29 mmol) of 3-benzyl-6-(4-fluorophenyl)-6-hydroxy-1,5-cis-3-azabicyclo[3.3.0]octane were dissolved in 250 ml of methanol and 2.0 g of palladium on carbon (10%) were added. A solution of 9.1 g (145 mmol) of ammonium formate in 11 ml of water was then added dropwise with stirring and the mixture was refluxed for a further 3 h after addition was complete. The catalyst was filtered off with suction and washed well with methanol, and the combined filtrates were concentrated to dryness. The residue was taken up in water, adjusted to pH 9–10 with ten percent sodiumhydroxide solution and extracted twice with dichloromethane. Drying and concentration of the organic phase yielded 5.4 g (84%) of yellowish oil.

c) 6-(4-Fluorophenyl)-1,5-cis-3-azabicyclo[3.3.0]oct-6-ene 6.9 g (31 mmol) of 6-(4-fluorophenyl)-6-hydroxy-1,5-cis-3-azabicyclo[3.3.0]octane were taken up in 50 ml of half-concentrated hydrochloric acid and the mixture was refluxed for 5 h. It was then diluted with water while cooling in ice, adjusted to pH 11 with concentrated sodium hydroxide solution and extracted twice with dichloromethane. Drying and concentration of the organic phase yielded a dark oil (5.9 g), which was purified by column chromatography (silica gel, eluent methanol/aqueous ammonia solution 95:5). 5.3 g (84%) of brown oil were obtained.

F. 6-(4-Fluorophenyl)-1,5-cis-3-azabicyclo[3.3.0]octane 5.3 g (26.1 mmol) of 6-(4-fluorophenyl)-1,5-cis-3-azabicyclo[3.3.0]oct-6-ene were dissolved in 100 ml of methanol and 1.0 g of palladium on carbon (10%) was added. The reaction mixture was catalytically hydrogenated under normal conditions. The catalyst was filtered off with suction and washed well with methanol, and the combined filtrates were concentrated to dryness. 4.4 g (82%) of product was isolated as an exo/endo diastereomer mixture, which was separated by column chromatography (silica gel, eluent methanol/ammonium hydroxide 90:10).

G. exo-7-Phenyl-1,5-cis-3-azabicyclo[3.3.0]octane

A reaction mixture of 9.9 g (50 mmol) of 3-benzyl-1,5-cis-3-azabicyclo[3.3.0]oct-6-ene (K. Miyajima, M. Takemoro and K. Achiwa, Chem. Pharm. Bull. 39 (1991) 3175), 14.0 ml (125 mmol) of iodobenzene, 0.9 g (4.0 mmol) of palladium(II) acetate, 2.1 g (8.0 mmol) of triphenylphosphine, 4.3 g (50 mmol) of piperidine and 2.3 g (50 mmol) of formic acid in 100 ml of dimethylformamide was heated at 80° C. for 6 h with good stirring. After concentrating the mixture in an oil pump vacuum, the residue was partitioned between water and methylene chloride, the mixture was acidified with ten percent hydrochloric acid, and the organic phase was concentrated after drying with sodium sulfate. The crude product was purified by column chromatography (silica gel, eluent ethyl acetate/n-hexane 1:1). 3.6 g (26%) of the N-benzyl derivative were isolated and converted by catalytic hydrogenation in a similar manner to Example F to the final product (yellow oil).

The following can be prepared in a similar manner (see Example O):

exo-7-(p-fluorophenyl)-1,5-cis-3-azabicyclo[3.3.0] octane

H. endo-6-p-Fluorophenyl-1,5-cis-3-azabicyclo[4.3.0]nonane a) endo-3-p-Fluorophenylcyclohex-4-ene-cis-1,2-dicarboxylic anhydride 53.0 g (358 mmol) of trans-1-p-fluorophenyl-1,3-butadiene in 100 ml of toluene were slowly heated to 100° C. with 34.3 g (350 mmol) of maleic anhydride while stirring well and the mixture was kept at this temperature for 1.5 h. After cooling, the mixture was concentrated to one half and the product was allowed to crystallize while cooling in an ice bath. The crystals were filtered off with suction and washed with a little cold toluene. 59 g (69%) of product of m.p. 88°–90° C. were isolated.

b) cis-3-p-Fluorophenyl-cis-1,2-bis(hydroxymethyl)-4-cyclohexene

A solution of 12.0 g (49 mmol) of endo-3-p-fluorophenylcyclohex-4-ene-cis-1,2-dicarboxylic anhydride in 60 ml of tetrahydrofuran was added dropwise at room temperature and with good stirring to 3.5 g (92 mmol) of lithium aluminum hydride in 170 ml of absolute tetrahydrofuran in the course of 45 min. After stirring for 1.5 h, the mixture was refluxed for a further 2 h. After cooling, ten percent sodium hydroxide solution was carefully added dropwise while cooling in ice and with good stirring, and the precipitated hydroxides were filtered off with suction. The filtrate was concentrated to dryness, and the residue was partitioned between ten percent sodium hydroxide solution and methyl t-butyl ether. The aqueous phase was re-extracted twice with methyl t-butyl ether, and the organic phase was then concentrated after drying with sodium sulfate. 8.9 g (77%) of product were isolated as a clear oil.

c) cis-3-p-Fluorophenyl-cis-1,2-bis(methanesulfonyloxymethyl)-cyclohex-4-ene 19.7 g (84 mmol) of cis-3-p-fluorophenyl-cis-1,2-bis(hydroxymethyl)cyclohex-4-ene in 70 ml of pyridine were added dropwise at 0° C. with good stirring to a solution of 28.6 g (250 mmol) of methanesulfonyl chloride in 100 ml of pyridine and the mixture was stirred for 2 h at 0° C. It was subsequently poured onto ice-water into which 64 ml of concentrated sulfuric acid had been introduced, and the mixture was extracted twice with methylene chloride. The organic phases were washed twice with ten percent sulfuric acid and concentrated after drying with sodium sulfate. 30.3 g (92%) of product were isolated as a pale oil.

d) 3-Benzylendo-6-p-fluorophenyl-1,5-cis-3-azabicyclo[4.3.0]-non-7-ene 21.8 g (56 mmol) of cis-3-p-fluorophenyl-cis-1,2-bis(methanesulfonyloxymethyl)cyclohex-4-ene were introduced in portions into 20 ml (183 mmol) of benzylamine with good stirring (exothermic reaction). The mixture was subsequently heated at 130° C. for a further 2 h. After cooling, 200 ml of methyl t-butyl ether were added to the reaction mixture, which was stirred until it crystallized. After filtering off the crystals with suction and washing with methyl t-butyl ether, the filtrate was washed twice with aqueous ammonia solution and the organic phase was concentrated after drying with sodium sulfate. The crude product (16.5 g) was purified by column chromatography (silica gel, eluent ethyl acetate/n-hexane 6:4). 10.5 g (61%) of product were isolated as a pale oil.

e) endo-6-p-Fluorophenyl-1,5-cis-3-azabicyclo[4.3.0]nonane 10.0 g (32 mmol) of 3-benzyl-endo-6-p-fluorophenyl-1,5-cis-3-azabicyclo[4.3.0]non-7-ene in 200 ml of methanol were catalytically hydrogenated at room temperature in the presence of 1.3 g of palladium on carbon (10%). After filtering off the catalyst with suction and washing with methanol, 7.8 g of crude product were isolated after concentration as a pale oil which was purified by column chromatography (silica gel, eluent methanol/aqueous ammonia solution 85:15). 4.6 g (66%) of product of m.p. 76°–78° C. were isolated.

The following can be prepared in a similar way:

f) endo-6-phenyl-1,5-cis-3-azabicyclo[4.3.0]nonane g) endo-6-p-trifluoromethylphenyl-1,5-cis-3-azabicyclo[4.3.0]nonane

I. endo-6-p-Fluorophenyl-1,5-cis-3-azabicyclo[4.3.0]non-7-ene 20 ml of ammonia were injected into a 0.3 l stirred autoclave containing 7.6 g (19.4 mmol) of cis-3-p-fluorophenyl-cis-1,2-bis-(methanesulfonyloxymethyl)cyclohex-4-ene in 100 ml of toluene and the mixture was heated at 150° C. for 5 h under autogenous pressure. The reaction mixture was then poured onto ice-water and the organic phase was washed with water after filtering off the insoluble components with suction. After drying and concentration, 4.4 g of crude product were isolated and purified by column chromatography (silica gel, eluent methanol/aqueous ammonia solution 85:15). 0.9 g (21%) of product were isolated as a colorless oil.

K. 6-p-Fluorophenyl-1,5-cis-3-azabicyclo[4.3.0]non-6-ene a) endo-3-p-Fluorophenylcyclohex-4-ene-cis-1,2-dicarboximide 50.0 g (338 mmol) of trans-1-p-fluorophenyl-1,3-butadiene in 100 ml of toluene were slowly heated to 100° C. with 32.0 g (330 mmol) of maleimide while stirring well and the mixture was kept at this temperature for 2 h. After cooling, it was concentrated to one half and the product was allowed to crystallize while cooling in an ice-bath. The crystals were filtered off with suction and washed with a little cold toluene. 69.7 g (86%) of product of m.p. 184°–186° C. were isolated.

b) 3-p-Fluorophenylcyclohex-3-ene-cis-1,2-dicarboximide 9.8 g (40 mmol) of endo-3-p-fluorophenylcyclohex-4-ene-cis-1,2-dicarboximide in 100 ml of dimethylformamide were treated in portions with 2.4 g (80 mmol) of sodium hydride (80%) with good stirring (exothermic reaction). The mixture was stirred for a further 2 h at 45° C. and subsequently poured onto ice-water after cooling. 100 ml of methyl t-butyl ether were added after acidifying with ten percent hydrochloric acid and the mixture was stirred vigorously. The pale solid was filtered off with suction, washed with a little methyl t-butyl ether and water and dried under reduced pressure at 50° C. The crude product was purified by column chromatography (silica gel, eluent methylene chloride/methanol 97:3). 6.7 g (68%) of product (main polar zone) of m.p. 197°–199° C. were isolated.

c) 6-p-Fluorophenyl-1,5-cis-3-azabicyclo[4.3.0]non-6-ene

A solution of 4.0 g (16.4 mmol) of 3-p-fluorophenylcyclohex-3-ene-cis-1,2-dicarboximide in 50 ml of tetrahydrofuran was added dropwise at room temperature and with good stirring to 1.96 g (51 mmol) of lithium aluminum hydride in 60 ml of absolute tetrahydrofuran in the course of 45 min. After stirring for 1.5 h the mixture was refluxed for a further 3 h. After cooling, ten percent sodium hydroxide solution was carefully added dropwise with ice-cooling stirring and the precipitated hydroxides were filtered off with suction. The filtrate was concentrated to dryness, and the residue was partitioned between water and methyl t-butyl ether at pH=10. The organic phase was extracted with five percent hydrochloric acid, rendered alkaline with concentrated sodium hydroxide solution and extracted twice with methyl t-butyl ether. After drying and concentration, 1.6 g (45%) of product were obtained as a pale oil.

The following can be prepared in a similar manner:

d) 6-phenyl-1,5-cis-3-azabicyclo[4.3.0]non-6-ene

L. exo-6-p-Fluorophenyl-1,5-cis-3-azabicyclo[4.3.0]nonane a) exo-3-p-Fluorophenylcyclohex-4-ene-cis-1,2-dicarboximide 15.0 g (61 mmol) of endo-3-p-fluorophenylcyclohex-4-ene-cis-1,2-dicarboximide in 100 ml of dimethylformamide were treated in portions with good stirring with 12.9 g (94 mmol) of finely pulverized potassium carbonate and the mixture was kept for 2 h at 100° C. and then poured onto ice-water after cooling. After acidifying with concentrated hydrochloric acid, it was extracted with methyl t-butyl ether and the organic phase was washed with ten percent hydrochloric acid. After drying and concentration, 18.1 g of crude product were isolated, which was washed with 50 ml of ether by stirring. 12.1 g (81%) of colorless crystals of m.p. 119°–121° C. were isolated. The configuration of the product was confirmed by the crystal structure analysis.

b) exo-6-p-Fluorophenyl-1,5-cis-3-azabicyclo[4.3.0]non-7-ene

A solution of 6.5 g (26 mmol) of 3-p-fluorophenylcyclohex-4-ene-cis-1,2-dicarboximide in 60 ml of tetrahydrofuran was added dropwise at room temperature and with good stirring to 3.2 g (84 mmol) of lithium aluminum hydride in 120 ml of absolute tetrahydrofuran within the course of 45 min. After stirring for 1.5 h, the mixture was refluxed for a further 3 h. After cooling, ten percent sodium hydroxide solution was carefully added dropwise with good stirring and with ice cooling and the precipitated hydroxides were filtered off with suction. The filtrate was concentrated to dryness, and the residue was partitioned between ten percent hydrochloric acid and methyl t-butyl ether. The aqueous phase was washed with methyl t-butyl ether, rendered alkaline with concentrated sodium hydroxide solution and extracted twice with methyl t-butyl ether. After drying and concentration, 3.6 g (64%) of product were isolated as a pale oil.

c) exo-6-p-Fluorophenyl-1,5-cis-3-azabicyclo[4.3.0]nonane

Obtained by catalytic hydrogenation of exo-6-p-fluorophenyl-1,5-cis-3-azabicyclo[4.3.0]non-7-ene according to the procedure of Example F: yield 89%.

The following can be prepared in a similar manner:

d) exo-6-phenyl-1,5-cis-3-azabicyclo[4.3.0]nonane

M. exo-7-Phenyl-1,5-cis-3-azabicyclo[4.3.0]non-8-ene a) exo-4-Phenylcyclohex-5-ene-cis-1,2-dicarboximide A mixture of 15.1 g (100 mmol) of cyclohex-4-ene-cis-1,2-dicarboximide, 28.0 ml (250 mmol) of iodobenzene, 1.8 g (8.0 mmol) of palladium(II) acetate, 2.1 g (8.0 mmol) of triphenylphosphine, 8.5 g (100 mmol) of piperidine and 4.6 g (100 mmol) of formic acid in 200 ml of dimethylformamide was heated at 80° C. for 6 h with good stirring. After concentration of the mixture in an oil pump vacuum, the residue was partitioned between water and methylene chloride, the mixture was acidified with ten percent hydrochloric acid and the organic phase was concentrated after drying with sodium sulfate. The crude product (31 g) was purified by column chromatography (silica gel, eluent ethyl acetate/n-hexane 1:1). 2 main fractions were isolated: the polar zone yielded 3.9 g (17%) of product as a yellowish oil.

b) exo-7-Phenyl-1,5-cis-3-azabicyclo[4.3.0]non-8-ene 1.0 g (26 mmol) of lithium aluminum hydride was added in portions to 3.0 g (17.2 mmol) of exo-4-phenylcyclohex-5-ene-cis-1,2-dicarboximide in 150 ml of tetrahydrofuran at room temperature and with good stirring. After stirring for 0.5 h, the mixture was refluxed for a further 3 h. After cooling, ten percent sodium hydroxide solution was carefully added dropwise with good stirring and with ice cooling and the precipitated hydroxides were filtered off with suction and washed with tetrahydrofuran. The filtrate was concentrated to dryness, and the residue was partitioned between water and methyl t-butyl ether at pH=10. After drying and concentration, 3.2 g of crude product were isolated as a dark oil. The crude product was purified by column chromatography (silica gel, eluent methylene chloride/methanol 1:1). 1.1 g (32%) of product were isolated as a pale oil.

N. 7-Phenyl-3-azabicyclo[4.3.0]non-1-ene a) 4-Phenylcyclohex-1-ene-1,2-dicarboximide The non-polar main fraction from column chromatography of Example M.a) yielded 3.2 g (15%) of product as a colorless oil/crystal mixture.

b) 7-Phenyl-3-azabicyclo[4.3.0]non-1-ene

In a similar manner to Example M.b), reduction with lithium aluminum hydride yielded 0.7 g (25%) of product as a pale oil.

O. exo-7-p-Fluorophenyl-1,5-cis-3-azabicyclo[4.3.0]nonane a) 4-p-Fluorophenylcyclohex-1-ene-1,2-dicarboximide A reaction mixture of 45.3 g (300 mmol) of cyclohex-4-ene-cis-1,2-dicarboximide, 82.5 ml (750 mmol) of p-bromofluorobenzene, 5.4 g (24 mmol) of palladium(II) acetate, 6.3 g (24 mmol) of triphenylphosphine, 29.7 ml (300 mmol) of piperidine and 11.4 ml (300 mmol) of formic acid in 600 ml of dimethylformamide was heated at 95° to 100° C. for 6 h with good stirring. After concentrating the mixture in an oil pump vacuum, the residue was partitioned between water and methylene chloride, the mixture was acidified with ten percent hydrochloric acid, the organic phase was washed with ten percent hydrochloric acid and the organic phase was concentrated after drying with sodium sulfate. The crude product (71 g) was stirred in 350 ml of ethyl acetate and the brown solid was filtered off with suction and washed with ethyl acetate. Concentration of the filtrate afforded 56 g of crude product, which was purified by column chromatography (silica gel, eluent ethyl acetate/n-hexane 40:60). 2 main fractions were isolated: the non-polar zone yielded 13.3 g of product which was washed with a 1:1 mixture of ethyl acetate and n-hexane by stirring. 8.9 g (12%) of product of m.p. 136°–137° C. were isolated.

b) 7-p-Fluorophenyl-3-azabicyclo[4.3.0]non-1-ene 4.5 g (118 mmol) of lithium aluminum hydride were added in portions to 9.4 g (38 mmol) of 4-p-fluorophenylcyclohex-1-ene-1,2-dicarboximide in 300 ml of tetrahydrofuran during the course of 45 min at room temperature and with good stirring. After stirring for 0.5 h, the mixture was refluxed for a further 6 h. After cooling, ten percent sodium hydroxide solution was carefully added dropwise with good stirring and with ice cooling and the precipitated hydroxides were filtered off with suction and washed with tetrahydrofuran. The filtrate was concentrated to dryness and the residue was partitioned between water and methyl t-butyl ether at pH=10. The organic phase was subsequently extracted twice with ten percent hydrochloric acid and the acidic aqueous phase was rendered alkaline again after this with concentrated sodium hydroxide solution. It was then extracted twice with methyl t-butyl ether. After drying and concentration, 1.8 g (22%) of product were isolated as a pale oil.

c) exo-4-p-Fluorophenylcyclohex-5-ene-cis-1,2-dicarboximide

The polar main fraction from column chromatography of Example O.a) yielded 9.2 g of product, which was digested in a little ether. 4.3 g (6%) of product of m.p. 139° to 142° C. were isolated.

d) exo-7-p-Fluorophenyl-1,5-cis-3-azabicyclo[4.3.0]non-8-ene

In a similar manner to Example O.b), reduction with lithium aluminum hydride yielded 2.4 g (63%) of product as a pale oil.

e) exo-7-p-Fluorophenyl-1,5-cis-3-azabicyclo[4.3.0]nonane

Catalytic hydrogenation in a similar manner to Example F yielded 2.2 g (92%) of product as a yellowish oil.

P. 6-Phenyl-1,5-cis-8-oxa-3,7-diazabicyclo[3.3.0]oct-6-ene 5.0 g (41 mmol) of benzaldehyde oxime in 50 ml of methylene chloride were treated with 6.8 g (41 mmol) of 1-trifluoroacetyl-3-pyrroline. 36.9 g (74 mmol) of a five percent sodium hypochlorite solution were then added dropwise while stirring well (exothermic reaction). After stirring for 2 h, the mixture was poured onto ice-water, rendered alkaline with concentrated ammonia solution and extracted twice with methylene chloride. The combined organic phases were washed with water and concentrated after drying with sodium sulfate. The crude product (13.1 g) was purified by column chromatography (silica gel, eluent methylene chloride). 3.5 g (30%) of the trifluoroacetyl derivative were isolated and were hydrolyzed during a further 30 min at room temperature in 2N methanolic sodium hydroxide solution to give the final product of m.p. 78°–80° C.

Reduction with sodium cyanoborohydride afforded exo/endo-6-phenyl-1,5-cis-8-oxa-3,7-diazabicyclo[3.3.0]octane as a pale oil.

The following can be prepared in a similar manner:

6-p-fluorophenyl-1,5-cis-8-oxa-3,7-diazabicyclo [3.3.0]oct-6-ene exo/endo-6-p-fluorophenyl-1,5-cis-8-oxa-3,7-diazabicyclo[3.3.0]octane

EXAMPLE 1

N-(2-[exo-6-Phenyl-7-methyl-1,5-cis-3,7-diazabicyclo[3.3.0]octan-3-yl]ethyl)-4-fluorobenzamide 2.5 g (12.4 mmol) of exo-6-phenyl-7-methyl-1,5-cis-3,7-diazabicyclo-[3.3.0]octan in 50 ml xylene were treated with 2.5 g (12.4 mmol) of N-(2-chloroethyl)-4-fluorobenzamide and with 1.7 g (12.4 mmol) of finely pulverized potassium carbonate and 0.5 g of potassium iodide and refluxed with good stirring for 2 h.

After cooling, the mixture was concentrated on a rotary evaporator and the residue was partitioned between methylene chloride and water.

The aqueous phase was re-extracted twice with methylene chloride and the organic phase was then concentrated after drying with sodium sulfate. The crude product (4.9 g) was purified by column chromatography (silica gel, eluent methylene chloride/methanol 95:5). 2.5 g (55%) of product of m.p. 108°–110° C. (hydrochloride) were obtained.

The following can be prepared in a similar manner:
2. N-(2-[endo-6-phenyl-7-methyl-1,5-cis-3,7-diazabicyclo [3.3.0]octan-3-yl]ethyl)-4-fluorobenzamide,
3. N-(2-[exo-6-p-fluorophenyl-7-methyl-1,5-cis-3,7-diazabicyclo[3.3.0]octan-3-yl]ethyl)-4-fluorobenzamide,
4. N-(2-[exo-6-p-trifluoromethylphenyl-7-methyl-1,5-cis-3,7-diazabicyclo[3.3.0]octan-3-yl]ethyl)benzamide,
5. N-(2-[exo-6-m-chlorophenyl-7-methyl-1,5-cis-3,7-diazabicyclo[3.3.0]octan-3-yl]ethyl)benzamide,
6. N-(2-[exo-6-p-methoxyphenyl-7-methyl-1,5-cis-3,7-diazabicyclo[3.3.0]octan-3-yl]ethyl)-4-chlorobenzamide,
7. N-(2-[exo-6-phenyl-7-methyl-1,5-cis-3,7-diazabicyclo [3.3.0]octan-3-yl]ethyl)naphthalene-1-carboxamide,
8. 1-(4-fluorophenyl)-4-[exo-6-p-fluorophenyl-7-methyl-1, 5-cis-3,7-diazabicyclo[3.3.0]octan-3-yl]butan-1-one,
9. 1-(4-fluorophenyl)-4-[exo-6-p-fluorophenyl-7-methyl-1, 5-cis-3,7-diazabicyclo[3.3.0]octan-3-yl]butan-1-ol.

EXAMPLE 10

N-(2-[exo-6-p-Fluorophenyl-1,5-cis-3-azabicyclo [4.3.0]non-3-yl]ethyl)benzamide 1.6 g (7.3 mmol) of exo-6-p-fluorophenyl-1,5-cis-3-azabicyclo[4.3.0]nonane in 50 ml of xylene were treated with 2.7 g (14.6 mmol) of N-(2-chloroethyl)benzamide and with 1.4 g (10.0 mmol) of finely pulverized potassium carbonate and 0.5 g of potassium iodide and refluxed with good stirring for 8 h.

After cooling, the mixture was concentrated on a rotary evaporator and the residue was partitioned between methylene chloride and water (pH=10).

The aqueous phase was re-extracted twice with methylene chloride and the organic phase was then concentrated after drying with sodium sulfate. The crude product (4.0 g) was purified by column chromatography (silica gel, eluent methylene chloride/methanol 93:7). 1.3 g (49%) of product of m.p. 160°–162° C. (maleate) were obtained.

EXAMPLE 11

1-(2-[exo-6-p-Fluorophenyl-1,5-cis-3-azabicyclo [4.3.0]non-3-yl]ethyl)naphthalene 1.6 g (7.3 mmol) of exo-6-p-fluorophenyl-1,5-cis-3-azabicyclo[4.3.0]nonane in 50 ml of xylene were treated with 1.7 g (7.3 mmol) of 1-(2-bromo)ethylnaphthalene and with 1.4 g (10.0 mmol) of finely pulverized potassium carbonate and 0.5 g of potassium iodide and refluxed with good stirring for 9 h.

After cooling, the mixture was concentrated on a rotary evaporator and the residue was partitioned between methylene chloride and water (pH=10).

The aqueous phase was re-extracted twice with methylene chloride and the organic phase was then concentrated after drying with sodium sulfate. The crude product (3.5 g) was purified by column chromatography (silica gel, eluent methylene chloride/methanol 96:4). 1.8 g (66%) of product of m.p. 99°–100° C. (decomposition, fumarate) were obtained.

The following can be prepared in a simmilar manner:
12. 1-(4-fluorophenyl)-4-[exo-6-p-fluorophenyl-1,5-cis-3-azabicyclo[4.3.0]non-3-yl]butan-1-one,
13. 1-(4-fluorophenyl)-4-[exo-6-p-fluorophenyl-1,5-cis-3-azabicyclo[4.3.0]non-3-yl]butan-1-ol,
14. N-(2-[exo-6-p-fluorophenyl-1,5-cis-3-azabicyclo[4.3.0] non-3-yl]ethyl)-2-(N-methyl)aminobenzamide,
15. N-(2-[exo-6-p-fluorophenyl-1,5-cis-3-azabicyclo[4.3.0] non-3-yl]ethyl)-5-chlorothien-2-ylcarboxamide,
16. N-(2-[exo-6-p-fluorophenyl-1,5-cis-3-azabicyclo[4.3.0] non-3-yl]ethyl)inden-3-carboxamide,
17. N-(2-[exo-6-phenyl-1,5-cis-3-azabicyclo[4.3.0]non-3-yl]ethyl)-4-fluorobenzamide,
18. N-(2-[exo-6-phenyl-1,5-cis-3-azabicyclo[4.3.0]non-3-yl]ethyl)naphthalene-1-carboxamide,
19. 1-(2-[exo-6-p-fluorophenyl-1,5-cis-3-azabicyclo[4.3.0] non-7-en-3-yl]ethyl)naphthalene,
20. 1-(4-fluorophenyl)-4-[exo-6-p-fluorophenyl-1,5-cis-3-azabicyclo[4.3.0]non-7-en-3-yl]butan-1-one,
21. N-(2-[exo-6-p-fluorophenyl-1,5-cis-3-azabicyclo[4.3.0] non-7-en-3-yl]ethyl)benzamide,
22. N-(2-[exo-6-p-fluorophenyl-1,5-cis-3-azabicyclo[4.3.0] non-7-en-3-yl]ethyl)inden-3-carboxamide,
23. N-(2-[exo-6-p-fluorophenyl-1,5-cis-3-azabicyclo[4.3.0] non-7-en-3-yl]ethyl)naphthalene-1-carboxamide,
24. N-(2-[exo-6-phenyl-1,5-cis-3-azabicyclo[4.3.0]non-7-en-3-yl]ethyl)-4-fluorobenzamide,
25. N-(2-[exo-6-phenyl-1,5-cis-3-azabicyclo[4.3.0]non-7-en-3-yl]ethyl)-3-chloro-1-benzothien-2-ylcarboxamide,
26. 1-(2-[6-p-fluorophenyl-1,5-cis-3-azabicyclo[4.3.0]non-6-en-3-yl]ethyl)naphthalene,
27. 1-(4-fluorophenyl)-4-[6-p-fluorophenyl-1,5-cis-3-azabicyclo[4.3.0]non-6-en-3-yl]butan-1-one, 28. 1-(4-fluorophenyl)-4-[6-p-fluorophenyl-1,5-cis-3-azabicyclo[4.3.0]non-6-en-3-yl]butan-1-ol,
29. N-(2-[6-p-fluorophenyl-1,5-cis-3-azabicyclo[4.3.0]non-6-en-3-yl]ethyl)-2-(N-methyl)aminobenzamide,
30. N-(2-[6-p-fluorophenyl-1,5-cis-3-azabicyclo[4.3.0]non-6-en-3-yl]ethyl)-5-chlorothien-2-yl-carboxamide,
31. N-(2-[6-p-fluorophenyl-1,5-cis-3-azabicyclo[4.3.0]non-6-en-3-yl]ethyl)benzamide,
32. N-(2-[6-phenyl-1,5-cis-3-azabicyclo[4.3.0]non-6-en-3-yl]ethyl)-3-chloro-1-benzothien-2-ylcarboxamide,
33. N-(2-[6-p-trifluoromethylphenyl-1,5-cis-3-azabicyclo[4.3.0]non-6-en-3-yl]ethyl)naphthalene-1-carboxamide,
34. N-(2-[6-p-fluorophenyl-1,5-cis-3-azabicyclo[4.3.0]non-6-en-3-yl]ethyl)inden-3-carboximide,
35. N-(2-[6-p-fluorophenyl-1,5-cis-3-azabicyclo[4.3.0]non-6-en-3-yl]ethyl)napthalene-1-carboxamide,
36. 1-(2-[endo-6-p-fluorophenyl-1,5-cis-3-azabicyclo[4.3.0]non-3-yl]ethyl)naphthalene,
37. 1-(4-fluorophenyl)-4-[endo-6-p-fluorophenyl-1,5-cis-3-azabicyclo[4.3.0]non-3-yl]butan-1-one,
38. 1-(4-fluorophenyl)-4-[endo-6-p-fluorophenyl-1,5-cis-3-azabicyclo[4.3.0]non-3-yl]butan-1-ol,
39. N-(2-[endo-6-p-fluorophenyl-1,5-cis-3-azabicyclo[4.3.0]non-3-yl]-2-(N-methyl)aminobenzamide,
40. N-(2-[endo-6-p-fluorophenyl-1,5-cis-3-azabicyclo[4.3.0]non-3-yl]ethyl)benzamide,
41. N-(2-[endo-6-p-fluorophenyl-1,5-cis-3-azabicyclo[4.3.0]non-3-yl]ethyl)-5-chlorothien-2-ylcarboxamide,
42. N-(2-[endo-6-phenyl-1,5-cis-3-azabicyclo[4.3.0]non-3-yl]ethyl)-4-fluorobenzamide,
43. N-(2-[endo-6-p-trifluoromethylphenyl-1,5-cis-3-azabicyclo[4.3.0]non-3-yl]ethyl)inden-3-carboxamide,
44. 2-(2-[endo-6-p-fluorophenyl-1,5-cis-3-azabicyclo[4.3.0]non-7-en-3-yl]ethyl)naphthalene,
45. N-(2-[endo-6-p-fluorophenyl-1,5-cis-3-azabicyclo[4.3.0]non-7-en-3-yl]ethyl)benzamide,
46. N-(2-[endo-6-p-fluorophenyl-1,5-cis-3-azabicyclo[4.3.0]non-7-en-3-yl]ethyl)-2-(N-methyl)aminobenzamide,
47. N-(2-[endo-6-p-fluorophenyl-1,5-cis-3-azabicyclo[4.3.0]non-7-en-3-yl]naphthalene-1-carboxamide,
48. 1-(2-[exo-7-p-fluorophenyl-1,5-cis-3-azabicyclo[4.3.0]non-8-en-3-yl]ethyl)naphthalene,
49. 1-(4-fluorophenyl)-4-[exo-7-p-fluorophenyl-1,5-cis-3-azabicyclo[4.3.0]non-8-en-3-yl]butan-1-one,
50. N-(2-[exo-7-p-fluorophenyl-1,5-cis-3-azabicyclo[4.3.0]non-8-en-3-yl]ethyl)benzamide,
51. N-(2-[exo-7-p-fluorophenyl-1,5-cis-3-azabicyclo[4.3.0]non-8-en-3-yl]ethyl)-5-chlorothien-2-ylcarboxamide,
52. N-(2-[exo-7-p-fluorophenyl-1,5-cis-3-azabicyclo[4.3.0]non-8-en-3-yl]ethyl)-3-chloro-1-benzothien-2-ylcarboxamide,
53. N-(2-[exo-7-phenyl-1,5-cis-3-azabicyclo[4.3.0]non-8-en-3-yl]ethyl)inden-3-carboxamide,
54. N-(2-[exo-7-phenyl-1,5-cis-3-azabicyclo[4.3.0]non-8-en-3-yl]ethyl)naphthalene-1-carboxamide,
55. 1-(2-[exo-7-p-fluorophenyl-1,5-cis-3-azabicyclo[4.3.0]non-3-yl]ethyl)naphthalene,
56. 1-(4-fluorophenyl)-4-[exo-7-p-fluorophenyl-1,5-cis-3-azabicyclo[4.3.0]non-3-yl]butan-1-one,
57. 1-(4-fluorophenyl)-4-[exo-7-p-fluorophenyl-1,5-cis-3-azabicyclo[4.3.0]non-3-yl]butan-1-ol,
58. N-(2-[exo-7-p-fluorophenyl-1,5-cis-3-azabicyclo[4.3.0]non-3-yl]ethyl)-2-(N-methyl)aminobenzamide,
59. N-(2-[exo-7-p-fluorophenyl-1,5-cis-3-azabicyclo[4.3.0]non-3-yl]ethyl)benzamide,
60. N-(2-[exo-7-p-fluorophenyl-1,5-cis-3-azabicyclo[4.3.0]non-3-yl]ethyl)-5-chlorothien-2-ylcarboxamide,
61. N-(2-[exo-7-p-fluorophenyl-1,5-cis-3-azabicyclo[4.3.0]non-3-yl]ethyl)naphthalene-1-carboxamide,
62. N-(2-[exo-7-p-fluorophenyl-1,5-cis-3-azabicyclo[4.3.0]non-3-yl]ethyl)inden-3-carboxamide,
63. 1-(2-[6-p-fluorophenyl-1,5-cis-3-azabicyclo[3.3.0]oct-6-en-3-yl]ethyl)naphthalene,
64. 1-(4-fluorophenyl)-4-[6-p-fluorophenyl-1,5-cis-3-azabicyclo[3.3.0]oct-6-en-3-yl]butan-1-one,
65. N-(2-[6-p-fluorophenyl-1,5-cis-3-azabicyclo[3.3.0]oct-6-en-3-yl]ethyl)benzamide,
66. N-(2-[6-p-fluorophenyl-1,5-cis-3-azabicyclo[3.3.0]oct-6-en-3-yl]ethyl)naphthalene-1-carboxamide,
67. 1-(2-[exo-6-p-fluorophenyl-1,5-cis-3-azabicyclo[3.3.0]octan-3-yl]ethyl)naphthalene,
68. 1-(4-fluorophenyl)-4-[exo-6-p-fluorophenyl-1,5-cis-3-azabicyclo[3.3.0]octan-3-yl]butan-1-ol,
69. N-(2-[exo-6-p-fluorophenyl-1,5-cis-3-azabicyclo[3.3.0]octan-3-yl]ethyl)benzamide,
70. N-(2-[exo-6-phenyl-1,5-cis-3-azabicyclo[3.3.0]octan-3-yl]ethyl)naphthalene-1-carboxamide,
71. N-(2-[exo-6-phenyl-1,5-cis-3-azabicyclo[3.3.0]octan-3-yl]ethyl)inden-3-carboxamide,
72. 1-(2-[endo-6-p-fluorophenyl-1,5-cis-3-azabicyclo[3.3.0]octan-3-yl]ethyl)naphthalene,
73. 1-(4-fluorophenyl)-4-[endo-6-p-fluorophenyl-1,5-cis-3-azabicyclo[3.3.0]octan-3-yl]butan-1-one,
74. N-(2-[endo-6-p-fluorophenyl-1,5-cis-3-azabicyclo[3.3.0]octan-3-yl]ethyl)benzamide,
75. N-(2-[endo-6-phenyl-1,5-cis-3-azabicyclo[3.3.0]octan-3-yl]ethyl)naphthalene-1-carboxamide,
76. 1-(2-[exo-7-p-fluorophenyl-1,5-cis-3-azabicyclo[3.3.0]octan-3-yl]ethyl)naphthalene,
77. 1-(4-fluorophenyl)-4-[exo-7-p-fluorophenyl-1,5-cis-3-azabicyclo[3.3.0]octan-3-yl]butan-1-one,
78. N-(2-[exo-7-p-fluorophenyl-1,5-cis-3-azabicyclo[3.3.0]octan-3-yl]ethyl)benzamide,
79. N-(2-[exo-7-phenyl-1,5-cis-3-azabicyclo[3.3.0]octan-3-yl]ethyl)naphthalene-1-carboxamide,
80. N-(2-[exo-7-phenyl-1,5-cis-3-azabicyclo[3.3.0]octan-3-yl]ethyl)inden-3-carboxamide,
81. N-(2-[exo-6-p-fluorophenyl-3-azabicyclo[3.1.0]hexan-3-yl]ethyl)-4-fluorobenzamide,
82. N-(2-[exo-6-phenyl-3-azabicyclo[3.1.0]hexan-3-yl]ethyl)-5-chlorothien-2-ylcarboxamide,
83. N-(2-[6,6-diphenyl-3-azabicyclo[3.1.0]hexan-3-yl]ethyl)naphth-1-ylcarboxamide,
84. N-(2-[exo-6-p-fluorophenyl-3-azabicyclo[3.1.0]hexan-3-yl]ethyl)-3-chloro-1-benzothien-2-ylcarboxamide,
85. N-(2-[exo-6-m-chlorophenyl-3-azabicyclo[3.1.0]hexan-3-yl]ethyl)-4-chlorobenzamide,
86. 1-(2-[6-p-fluorophenyl-1-5-cis-8-oxa-3,7-diazabicyclo[3.3.0]oct-6-en-3-yl]ethyl)naphthalene,
87. N-(2-[6-p-fluorophenyl-1-5-cis-8-oxa-3,7-diazabicyclo[3.3.0]oct-6-en-3-yl]ethyl)benzamide,
88. N-(2-[6-p-fluorophenyl-1-5-cis-8-oxa-3,7-diazabicyclo[3.3.0]oct-6-en-3-yl]ethyl)naphthalene-1-carboxamide,
89. N-(2-[6-p-fluorophenyl-1-5-cis-8-oxa-3,7-diazabicyclo[3.3.0]oct-6-en-3-yl]ethyl)inden-3-carboxamide,
90. 1-(2-[exo/endo-6-p-fluorophenyl-1-5-cis-8-oxa-3,7-diazabicyclo[3.3.0]octan-3-yl]ethyl)naphthalene,
91. N-(2-[exo/endo-6-p-fluorophenyl-1-5-cis-8-oxa-3,7-diazabicyclo[3.3.0]octan-3-yl]ethyl)benzamide,
92. 1-(2-[6-phenyl-1-5-cis-8-oxa-3,7-diazabicyclo[3.3.0]oct-6-en-3-yl]ethyl)naphthalene,
93. N-(2-[6-phenyl-1-5-cis-8-oxa-3,7-diazabicyclo[3.3.0]oct-6-en-3-yl]ethyl)benzamide.

We claim:
1. An N-substituted 3-azabicycloalkane derivative of the formula I

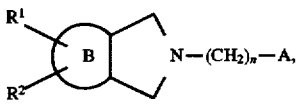

I where
- B is a 3-, 5- or 6-membered ring which can contain 1 nitrogen atom and/or 1 oxygen atom and possibly one double bond,
- $R^1$ is a phenyl group which is unsubstituted or mono- or disubstituted by halogen atoms or $C_1$–$C_4$-alkyl, trifluoromethyl, hydroxyl, $C_1$–$C_4$-alkoxy, amino, monomethylamino, dimethylamino, cyano or nitro groups,
- $R^2$ is a hydrogen atom or a $C_1$–$C_4$-alkyl radical,
- n is the number 2, 3 or 4,
- A is a hydrogen atom or one of the radicals

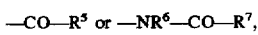

- $R^5$ is a phenyl group which is unsubstituted or mono- or disubstituted by fluorine, chlorine, bromine or a hydroxyl, nitro, amino, $C_{1-4}$-alkanoylamino, $C_{1-4}$-alkylamino, $C_1$–$C_4$-alkyl or methoxy group or a naphthyl group which is unsubstituted or substituted by fluorine or chlorine,
- $R^6$ is a hydrogen atom or a methyl group, and
- $R^7$ is a phenyl group which is mono- or disubstituted by fluorine, chlorine, bromine, $C_1$–$C_4$-alkyl, hydroxyl or methoxy or monosubstituted by nitro, cyano, trifluoromethyl, amino, $C_1$–$C_4$-alkylamino or di-$C_1$–$C_4$-alkylamino or a thienyl, naphthyl, benzothienyl or indenyl group which is unsubstituted or substituted by fluorine, chlorine or nitro, and their salts with physiologically tolerable acids.

2. The compound of claim 1, wherein
- B is a 5- or 6-membered ring which can contain one double bond,
- $R^1$ is a phenyl group which is unsubstituted or monosubstituted by halogen atoms,
- $R^2$ is hydrogen,
- n is 2, and
- A is —NH—CO—N-phenyl.

3. A method of treating nervous disorders in a patient in need thereof which comprises: administering to the patient an effective amount of a compound of the formula I as defined in claim 1.

* * * * *